United States Patent [19]
Vera

[11] Patent Number: 5,135,518
[45] Date of Patent: Aug. 4, 1992

[54] HEAT-RETENTIVE WET COMPRESS

[76] Inventor: Barbara Vera, 259 Oakville Ave., 42-B, Waterbury, Conn. 06708

[21] Appl. No.: 573,738

[22] Filed: Aug. 28, 1990

[51] Int. Cl.⁵ .......................... A61F 7/00; A61N 00/00
[52] U.S. Cl. ..................................... 604/291; 602/41; 602/57; 602/58
[58] Field of Search ................. 604/291, 304; 128/155, 128/156, 82.1; 602/14, 54, 57, 211, 52, 54, 55, 58, 59

[56] References Cited

U.S. PATENT DOCUMENTS

| | | | |
|---|---|---|---|
| 414,967 | 11/1889 | Berns | 604/304 |
| 1,602,344 | 10/1926 | Eagle | 604/304 |
| 1,753,106 | 3/1930 | Barth | 128/155 |
| 1,852,040 | 3/1932 | Blank | 604/304 |
| 2,344,021 | 4/1944 | Bouziane | 604/304 |
| 3,674,027 | 7/1972 | Fleischmajer | 604/304 |
| 3,871,376 | 3/1975 | Kozak | 604/291 |
| 3,929,131 | 12/1975 | Hardwick | 604/291 |
| 3,951,133 | 3/1976 | Reese | 128/736 |
| 4,302,500 | 11/1981 | Flora | 128/156 |
| 4,503,098 | 3/1985 | Potts | 604/381 |

Primary Examiner—Randall L. Green
Assistant Examiner—R. Clarke
Attorney, Agent, or Firm—Abdallah & Muckelroy

[57] ABSTRACT

A medical compress for hot or warm moist heat treatment. The compress is a multi-layered structure having a body of absorbent material sandwiched between a porous, liquid permeable layer and a liquid impermeable, heat-retentive layer, and a plurality of adhesive tabs disposed about the periphery of the compress. The heat-retentive layer maintains the compress at a desired temperature for the period of a treatment cycle. The compress is preferably biodegradable and microwavable to eliminate the bulky equipment now used in hydroculator therapy.

9 Claims, 2 Drawing Sheets

HEAT-RETENTIVE WET COMPRESS

BACKGROUND OF THE INVENTION

The present invention generally relates to wet compresses and more specifically to a wet compress for moist heat treatments and saline soaks.

Hot and warm compresses are used to treat a variety of ailments including inflammation, hematomas, arthritis, swollen joints, back spasms and contusions. Salinized hot or warm compresses are also used during pre-surgical or post-surgical procedures for saline soaks in the treatment of infected wounds and the like. The utility of the hot and warm compresses of the prior art is generally limited by two problems: (1) cumbersome and burdensome means of heating the compress, and (2) patient discomfort.

Hot and warm compresses in the prior art are generally prepared utilizing hydroculator packs and hot towels. Hydroculator packs are canvas-covered receptacles stuffed with horse hair or the like which are heated in a large pot of boiling water. The packs get very hot and often drip hot water so the patient must be protected when the compress is applied. This is usually done by wrapping the hydroculator packs in numerous towels. Heating the compress is inconvenient to the patient and to the treating medical professional. The required machinery must be stored in a central supply room and transported to each patient's relatively small room when a hot or warm compress is ordered. The packs are generally left in water at the patient's bedside for several days where additional water is added as the pack is reheated. This procedure increases the opportunity for bacteria to form in the heating tank and in the hydroculator pack. For home use, the hydroculator packs are usually stored frozen until needed and have to be heated in a large kettle of boiling water. Thus, a considerable amount of time is used in both instances to sufficiently heat the hydroculator packs. Generally a large number of towels are used in hydroculator therapy which must be laundered and further adds to the weight of equipment required. Also, a fire hazard is created in the patient's room since the heating equipment must be plugged into an electrical outlet. There is also a large cost for electricity associated with this means of preparing a hot or warm compress because the machinery must be plugged in from early morning to late evening. The technician or nurse operating the equipment wastes valuable time waiting for the equipment to heat the compress. The patient is further inconvenienced and made to feel uncomfortable because he/she generally feels that visitors are not welcomed during this procedure and thus oftentimes refuses the treatment.

Because of the large number of towels needed to wrap around the hydroculator packs, hot or warm compresses of the prior art are generally heavy and unwieldy for the patient to whom the compress is being applied. Because of the weight of the prior art heatpacks the patient is often required to remain stationary during treatment for twenty to thirty minutes, the normal cycle for heat treatments, and depending upon the part of the body being treated the patient may have to lay in an uncomfortable position. The weight of the hot or warm compresses of the prior art is particularly problematic in intravenous therapy where most antibiotics are given intravenously thus facilitating the occurrence of irritations and the start of phlebitis. Generally a warm face cloth is used which is covered by a towel and an incontinence pad and is taped or wrapped with plastic wrap to keep it warm. However, this operation generally fails to keep the face cloth warm and furthermore is cumbersome for the patient. Saline soak treatments further require that a sterile basin be obtained from central supply and brought to the patient's room. The bottle of saline is then placed in a sink of hot water or in a large basin to heat the saline before pouring it onto the lesion. If treating an abdominal wound the patient must remain exposed during treatment and a new gauze must be used with each application of the compress to the wound, the spent gauze being discarded in a contaminated waste container. Application of the gauze is usually done by the patient every fifteen to twenty minutes giving rise to opportunities for infection from the unsterile hands of the patient.

Various compresses have been disclosed in the prior art. U.S. Pat. No. 414,967 to Berns discloses a therapeutic pad that retains moisture and heat comprising a outer casing of porous material filled with moss. U.S. Pat. No. 1,602,344 to Eagle discloses a medicating compress that includes a layer of moisture-proof and insulating material to retain heat beneath the compress when it is positioned adjacent the body. In U.S. Pat. No. 3,674,027 to Fleischmajer a multi-layered disposable, dermatological compress is disclosed having a fluid reservoir layer, an absorbent layer disposed to one side of the fluid reservoir layer having an evaporation surface, and a smooth, water permeable application layer disposed to the opposite side of the fluid reservoir layer. The Fleischmajer disclosure teaches that the compress may be heated by placing the compress in a sealed bag and putting it into hot water, or into boiling water allowing time for cooling to obtain the desired temperature, as known for hydroculator therapy. A surgical bandage that includes a compress and adhesive attachment means is shown in U.S. Pat. No. 1,852,040 to Blank. A surgical bandage that includes a compress for stopping the flow of blood from a wound is shown in U.S. Pat. No. 2,344,021 to Bouziane.

As can be understood from the foregoing, there are numerous problems associated with the present methods of preparing and applying a hot or warm compress that have not been resolved by the prior art, the foregoing problems not being exclusive. Thus there remains a need within the art for a more efficient, cost effective and comfortable means of preparing and applying a hot or warm wet compress or saline soak that results in greater patient comfort and mobility and in greater treatment effectiveness.

SUMMARY OF THE INVENTION

The present invention discloses a medical compress that is biodegradable, disposable, lightweight and attachable to a patient by adhesive means. The medical compress of the present invention is microwavable and includes a heat-retentive plastic layer disposed to one side of the compress which provides the source of heat for moist heat treatments and saline soaks.

The medical compress of the present invention comprises a body of liquid absorbent material having a thin layer of plastic material disposed to one side of the absorbent material and a soft, woven fabric disposed to the opposite side of the absorbent material. A plurality of attachment tabs are disposed about the periphery of the compress, preferably formed from non-allergic silk tape, which include an adhesive film on one side of the attachment tabs. The adhesive film of the attachment tabs engages a tab liner fixedly attached to the upper surface of the woven fabric when the tabs are folded over the woven fabric which prevents the adhesive film from peeling away the fibers of the woven fabric when readied for attachment to the patient's skin. In the absence of wound exudate the compress can be re-used whereupon the attachment tabs are re-engaged to the tab liner for storage. A further embodiment of the present invention includes visual temperature indicia means to signal when the compress is heated to a desired temperature.

An object of the present invention is to provide a medical compress that can be used for moist heat treatments and saline soaks.

Another object of the present invention is to provide a medical compress that eliminates the burdensome heating equipment known in the prior art for preparation of a hot or warm compress in hydroculator therapy.

It is also an object of this invention to provide a medical compress that can be stored in a dry condition and microwaved for moist heat treatments.

Another object of the present invention is to provide a lightweight, hot or warm compress that can be worn with the patient unexposed and disposed in various positions or ambulatory during treatment.

A further object of the medical device of the present invention is to provide a hot or warm compress which retains its heat for the duration of a normal treatment cycle.

Another object of this invention is to provide a compress that can be re-used in the absence of draining wounds.

A still further object of this invention is to provide a cost effective, efficient means of preparing a hot or warm compress.

It is also an object of this invention to provide a medical compress that can be conveniently used in chiropractic offices, in sports medicine treatments, for in-home treatment, as well as in hospitals.

Another object of the present invention is to provide a medical compress that increases the safety of handling compresses containing bodily fluids.

These and other objects and advantages of the present invention will be apparent to those skilled in the art from the following description of a preferred embodiment, drawings and appended claims.

DESCRIPTION OF A PREFERRED EMBODIMENT

Figure 1:
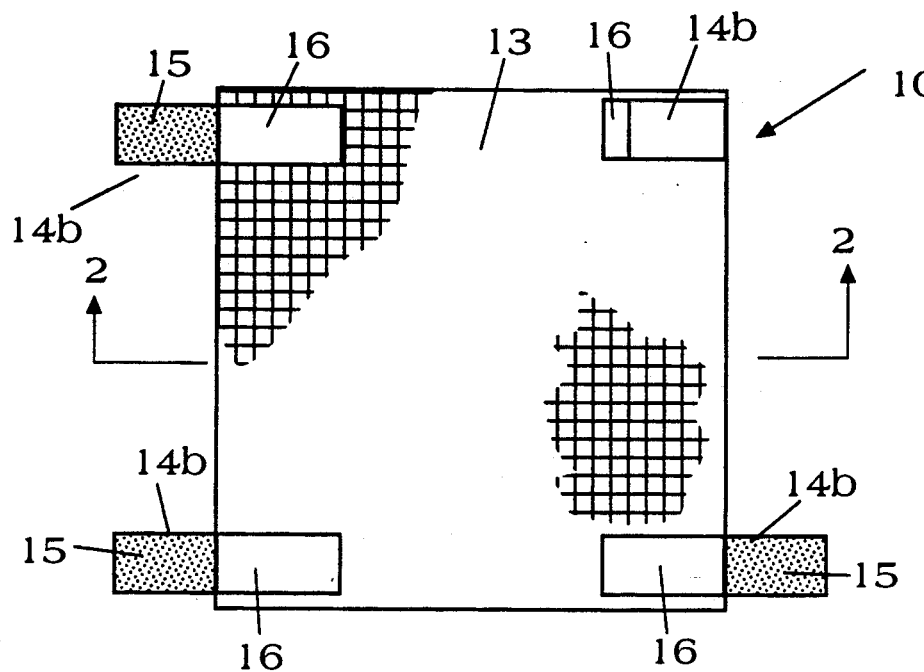
FIG. 1 is a plan view of the inside surface of a medical compress constructed in accordance with the teachings of the present invention.

FIG. 1 illustrates a plan view of a first embodiment of the medical compress 10 of the present invention. Medical compress 10 is shown having an essentially square configuration, however, this is for illustration only and it is to be understood that the compress 10 may be any of a wide variety of sizes, shapes, thicknesses, etc. for application to various parts of the body, depending on the particular requirements.

Figure 2:
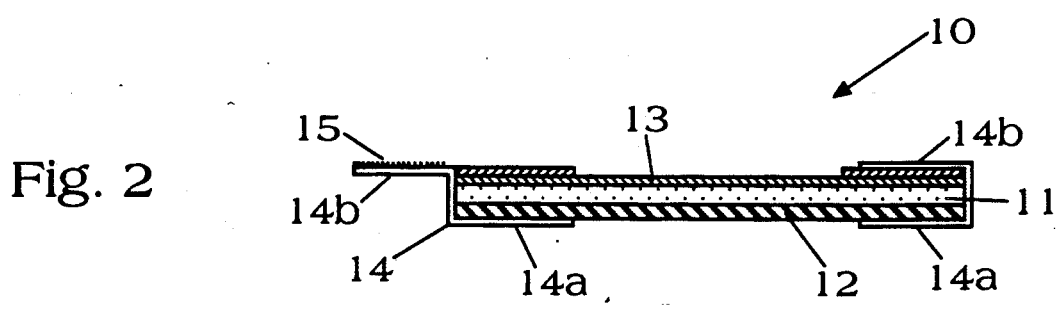
FIG. 2 is a cross-sectional view taken along line 2—2 of FIG. 1.

Referring to FIGS. 1 and 2 it can be seen that medical compress 10 is a multi-layered structure generally including a body of liquid absorbent material 11 having an inside surface and an outside surface. The terms inside surface and outside surface are used to distinguish the portions of the compress 10 which are oriented toward the patient's skin and away from the patient's skin, respectively, when the compress 10 is applied, and may alternatively be understood as a top surface and a bottom surface. A layer of heat retentive material 12 is disposed adjacent to the outside surface of said body of liquid absorbent material 11, and a layer of woven fabric 13 disposed adjacent to the inside surface of said body of liquid absorbent material 11. A plurality of attachment tabs 14 are disposed in spaced relationship about the periphery of the multi-layered structure of the compress 10. A first end 14a of each attachment tab 14 is fixedly attached to the outside surface of the heat retentive material 12. A second end 14b of said attachment tab 14 extends outwardly from said multi-layered structure and includes an adhesive film 15 on the inside surface of said second end 14b of said attachment tab 14. Attachment tab liners 16 for each attachment tab 14 are fixedly attached to the inside surface of the layer of woven fabric 13 in a manner such that when the second end 14b of said attachment tab 14 is folded over the layer of woven fabric 13, the stored position of the attachment tab 14, all portions of the adhesive film 15 contact the respective attachment tab liner 16. By this construction the adhesive film 15 is prevented from peeling away fibers of the woven fabric 13 thereby extending the life of the adhesive film 15 and facilitating adherence of the attachment tab 14 to the patient's skin. The second end 14b of said attachment tab 14 is formed with a marginally shorter length than said attachment tab liner 16 for easy removal of said second end 14b from said liner 16. The respective peripheral edges of the body of absorbent material 11, layer of heat retentive material 12 and layer of woven fabric 13 are fixedly sealed to one another to provide a leakproof and integral structure.

Medical compress 10 is preferably formed from biodegradable and disposable materials. The layer of woven material 13 is preferably a soft fabric that will prevent irritation of the patient's skin and provide comfort to the treated area. The heat retentive layer 12 is preferably a pliable and liquid impermeable plastic, for example the plastic material utilized in disposable diapers, having a heat modulus sufficient to retain the compress 10 at a desired temperature for twenty to thirty minutes, the generally useful period for a heat treatment cycle. The compress 10 should also be microwavable. Attachment tabs 14 are preferably formed from a non-allergic, breathing tape, for example BIOSPORE silk tape as manufactured by the 3M Company.

Figure 3:
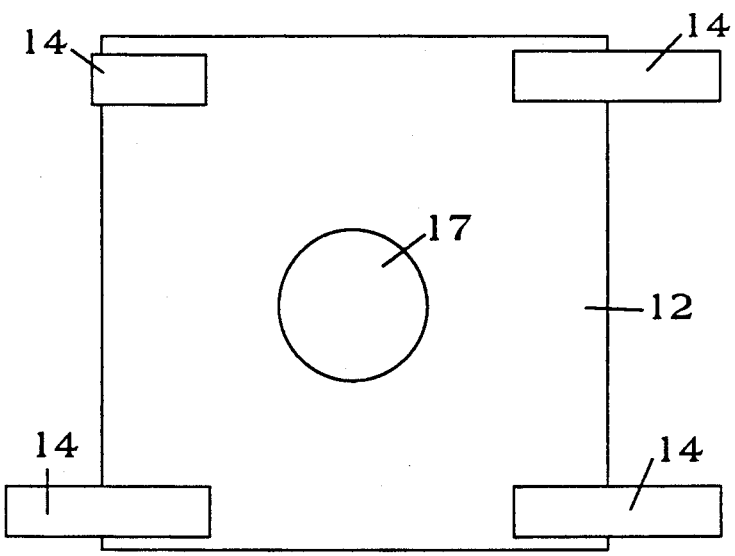
FIG. 3 is a plan view of the outside surface of the medical compress shown in FIGS. 1 and 2.

As can be seen in FIG. 3, medical compress 10 includes visual temperature indicia means 17 disposed on the outside surface of the heat-retentive layer 12 which indicates visually when the compress 10 has been heated to a desired temperature by changing colors. Said temperature indicia means 17 may be a heat-sensitive dye or the like.

As previously noted, when the compress 10 is stored the second ends 14b of the attachment tabs 14 are disposed overlapping the respective attachment tab liners 16. The compress 10 of the present invention, unlike the hydroculator packs of the prior art, need not be frozen prior to use and can be stored in a dry condition, preferably in a sterile package. For preparation and application of a hot or warm compress, the absorbent material 11 is first wetted by pouring water over the porous, layer of woven fabric 13. The compress 10 is then placed into a microwave oven and heated at the oven's lowest setting until the temperature indicia means 17 changes color. The compress 10 is then applied to the patient by pulling the second ends 14b of the attachment tabs 14 from the attachment tab liners 16 and sealing the adhesive means 15 adjacent to the patient's skin. Since the compress 10 retains heat at the desired temperature for the generally useful period of a complete treatment cycle, it need not be changed during treatment thereby eliminating potential infection from unsterile hands. Furthermore, the lightweight compress 10 of the present invention permits the patient to move about or assume a comfortable position during the treatment cycle.

For a warm saline soak, useful for treatment of an infected wound, the absorbent material 11 is wetted with a saline solution, microwaved and applied to the wound of the patient using the adhesive film 15 of the attachment tabs 14.

Figure 4:
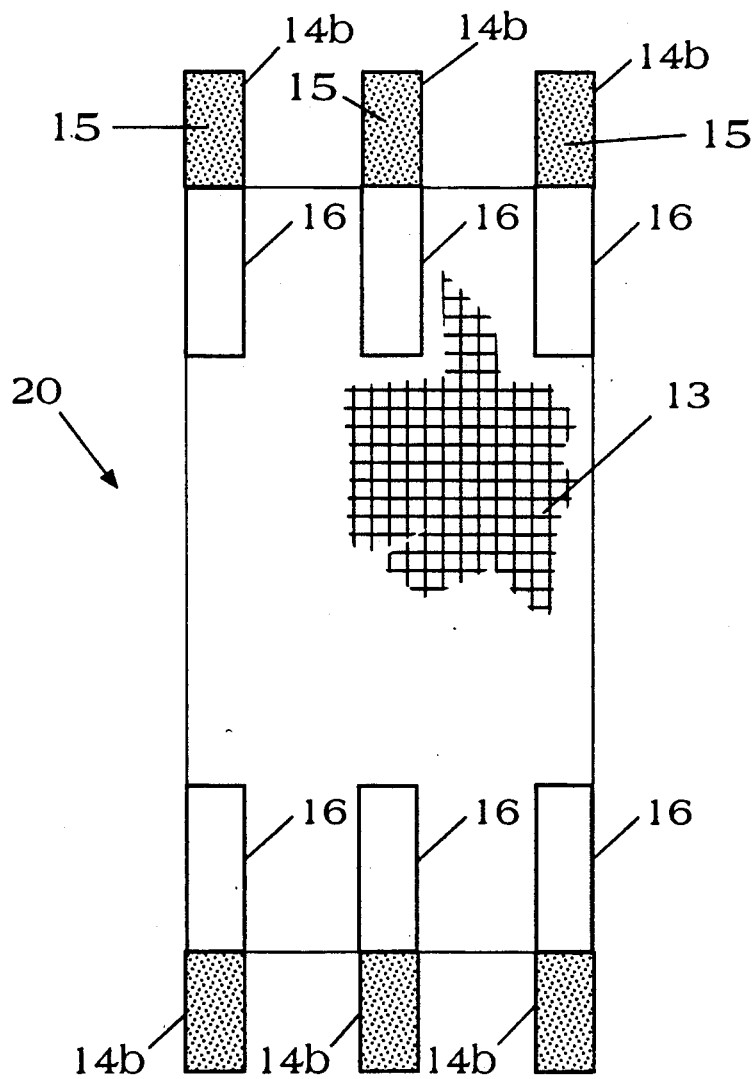
FIG. 4 is a plan view of the inside surface of a second embodiment of the medical compress of the present invention.

FIG. 4 illustrates a second embodiment of the medical compress 20 of the present invention wherein the multi-layered portion of the compress 20 is formed in an elongated, rectangular shape. Attachment tabs 14 and attachment tab liners 16 are disposed at the respective ends of said multi-layered portion as heretofore described. The second embodiment of the medical compress 20 illustrates a further advantage of the present invention over the prior art, whereas in the prior art the heat source for the compress, the hydroculator pack, is centrally disposed within a plurality of towels, the compress 20 of the present invention provides an extended heat source which can be wrapped around a patient's arm or leg, for example, or disposed in various orientations upon the patient's body to treat a larger area with directed moist heat.

The medical compress 10 of the present invention can also be used as a wound dressing by attaching the compress 10 to a patient's body in a dry condition. Where wound exudate is present, the body of absorbent material 11 will absorb the exudate. In the absence of wound exudate, the compress 10 can be re-used on the patient.

Therefore in view of the foregoing I claim:

1. A medical compress for moist heat therapy comprising
    a body of liquid absorbent material having an inside surface and an outside surface;
    a layer of heat-retentive material disposed adjacent to the outside surface of said body of liquid absorbent material, said heat-retentive material extending over at least a portion of the outside surface of said body of liquid absorbent material; and
    a layer of woven fabric disposed adjacent to the inside surface of said body of liquid absorbent material, said woven fabric extending over at least a portion of the inside surface of said body of liquid absorbent material,
    said body of liquid absorbent material, said layer of heat-retentive material and said layer of woven fabric being sealed together at the respective peripheral edges thereof;
    a plurality of attachment tab liners fixedly attached to the inside surface of said layer of woven fabric adjacent to respective attachment tabs; and
    a plurality of attachment tabs having a first end fixedly attached to said layer of heat-retentive material and a second end extending from said layer of heat-retentive material, said second end of said attachment tab having an adhesive film disposed on the inside surface thereof the inside surface of said second end being selectively disposable in bearing contact with respective adjacently-disposed attachment tab liners.

2. A medical compress as described in claim 1 wherein said layer of heat-retentive material has a heat modulus sufficient to retain the compress at a desired temperature for a minimum of twenty minutes.

3. A medical compress as described in claim 1 wherein said layer of heat-retentive material is a liquid impermeable material.

4. A medical compress as described in claim 1 further including visual temperature indicia means disposed on said layer of heat-retentive material.

5. A medical compress for moist heat therapy comprising
    a body of liquid absorbent material having a top surface and a bottom surface;
    a layer of liquid impermeable, heat-retentive material disposed adjacent to the bottom surface of said body of liquid absorbent material, said layer of heat-retentive material extending over at least a portion of the bottom surface of said body of liquid absorbent material and having a heat modulus sufficient to retain the compress at a desired temperature for a minimum of twenty minutes;
    a layer of soft, non-irritating and liquid permeable material disposed adjacent to the top surface of said body of liquid absorbent material, said liquid permeable material extending over at least a portion of the top surface of said body of liquid absorbent material,
    the peripheral edges of the respective body of liquid absorbent material, layer of heat-retentive material and layer of liquid permeable material being sealed together;
    a plurality of attachment tab liners fixedly attached to the top surface of said layer of liquid permeable material adjacent to respective attachment tabs; and
    a plurality of attachment tabs corresponding in number to said attachment tab liners and disposed adjacent thereto, said attachment tabs having a first end fixedly attached to said layer of heat-retentive material and a second end freely disposed therefrom having adhesive means disposed thereon.

6. A medical compress as described in claim 5 further including visual temperature indicia means.

7. A medical compress as described in claim 6 wherein said layer of adsorbent material, said layer of heat-retentive material and said layer of liquid permeable material are biodegradable.

8. A medical compress as described in claim 7 wherein said compress is microwaveably without physical destruction of the several layers of material in the medical compress.

9. A medical compress as described in claim 8 wherein said attachment tabs are formed from non-allergic, breathing material.

* * * * *